United States Patent
Campagna et al.

(10) Patent No.: US 10,082,552 B2
(45) Date of Patent: Sep. 25, 2018

(54) SIGNAL SELECTION OF RECEIVED SIGNALS IN MRI LOCAL RECEPTION ANTENNAS UTILIZING METADATA AND ANALOG-DIGITAL (A/D) CONVERTER CHIPS

(71) Applicants: Swen Campagna, Engelthal (DE); Stephan Stöcker, Baiersdorf (DE)

(72) Inventors: Swen Campagna, Engelthal (DE); Stephan Stöcker, Baiersdorf (DE)

(73) Assignee: Siemens Aktiengesellschaft, München (DE)

( * ) Notice: Subject to any disclaimer, the term of this patent is extended or adjusted under 35 U.S.C. 154(b) by 873 days.

(21) Appl. No.: 14/560,959

(22) Filed: Dec. 4, 2014

(65) Prior Publication Data

US 2015/0160318 A1    Jun. 11, 2015

(30) Foreign Application Priority Data

Dec. 10, 2013   (DE) ................. 10 2013 225 484

(51) Int. Cl.
*G01R 33/32* (2006.01)
*G01R 33/56* (2006.01)
(Continued)

(52) U.S. Cl.
CPC ......... *G01R 33/5608* (2013.01); *G01R 33/32* (2013.01); *G01R 33/3621* (2013.01); *A61B 5/055* (2013.01)

(58) Field of Classification Search
USPC ............................ 324/300–322; 600/407–435
See application file for complete search history.

(56) References Cited

U.S. PATENT DOCUMENTS 8,749,238 B2* 6/2014 Biber ................. G01R 33/3621
                                                            324/318
8,994,374 B2* 3/2015 Albsmeier ......... G01R 33/3692
                                                            324/318
(Continued)

FOREIGN PATENT DOCUMENTS

CN           101478067 A        7/2009
CN           101688906 A        3/2010
(Continued)

OTHER PUBLICATIONS

German Office Action cited in DE102013225484.9, dated Jul. 30, 2014.
(Continued)

*Primary Examiner* — Melissa Koval
*Assistant Examiner* — Tiffany Fetzner
(74) *Attorney, Agent, or Firm* — Lempia Summerfield Katz LLC (57) ABSTRACT

The embodiments relate to signal selection devices for reception antennas. The signal selection device includes a plurality of signal inputs for the reception of signals from the reception antennas via an interface arrangement, and a plurality of signal outputs for the output of altered signals from the reception antennas. The signal selection device is used for selecting/reducing received signals from the reception antennas and forwarding them to an image processing device. The signal selection device contains a plurality of A/D converter chips, a plurality of digital selection chips, and at least physical and/or logical portions of a control unit. The received signals from the reception antennas are fed into the plurality of A/D converter chips via a plurality of signal inputs, are converted into digital data streams, and are supplied to the digital selection chips via signal outputs of the A/D converter chips.

18 Claims, 4 Drawing Sheets

(51) Int. Cl.
*G01R 33/36* (2006.01)
*A61B 5/055* (2006.01)

(56) References Cited

U.S. PATENT DOCUMENTS

| | | | | |
|---|---|---|---|---|
| 9,547,064 B2* | 1/2017 | Biber | ............... | G01R 33/583 |
| 2009/0174498 A1 | 7/2009 | Xing et al. | | |
| 2012/0187949 A1* | 7/2012 | Biber | ............... | G01R 33/3621 |
| | | | | 324/322 |
| 2012/0249140 A1* | 10/2012 | Albsmeier | ......... | G01R 33/3692 |
| | | | | 324/309 |
| 2013/0082707 A1* | 4/2013 | Biber | ............... | G01R 33/583 |
| | | | | 324/309 |
| 2015/0160318 A1* | 6/2015 | Campagna | ......... | G01R 33/3621 |
| | | | | 324/309 |
| 2015/0287166 A1* | 10/2015 | Cerny | ............... | G02B 27/0172 |
| | | | | 345/423 |
| 2016/0033591 A1* | 2/2016 | Leussler | ............. | G01R 33/288 |
| | | | | 324/309 |

FOREIGN PATENT DOCUMENTS

| | | |
|---|---|---|
| CN | 102736042 A | 10/2012 |
| JP | 2006187405 A | 7/2006 |
| JP | 2007209658 A | 8/2007 |
| WO | WO2008155703 A1 | 12/2008 |

OTHER PUBLICATIONS

Chinese Office Action for Chinese Application No. 201410584646.9, dated Jun. 25, 2018, with English Translation.

\* cited by examiner

SIGNAL SELECTION OF RECEIVED SIGNALS IN MRI LOCAL RECEPTION ANTENNAS UTILIZING METADATA AND ANALOG-DIGITAL (A/D) CONVERTER CHIPS

CROSS-REFERENCE TO RELATED APPLICATIONS

This application claims the benefit of DE 10 2013 225 484.9, filed on Dec. 10, 2013, which is hereby incorporated by reference in its entirety.

TECHNICAL FIELD

The embodiments relate to an apparatus and a method for signal selection for the capture of received signals for reception antennas for a number of local coils of a reception device in a magnetic resonance imaging scanner (MRT). Furthermore, the embodiments relate to a local coil and also a magnetic resonance imaging scanner that are operated with the signal selection.

BACKGROUND

In order to produce MRT images having the best possible signal-noise ratio (SNR), reception antennas have been placed as close as possible to the object to be measured (e.g., patient or subject). These are what are known as local coils, which may be in the form of reception coils but additionally may also be transmission coils.

For the user of the MRT, a local coil is a physical unit that he may position on, below or against the patient. The physical unit may have a plurality of logical subunits, the coil elements, which the user may individually select or deselect for the measurement, for example. A coil element in turn may combine a plurality of reception antennas that produce the individual MRT signals (the "raw data"), which are ultimately used in the MRT imaging as single and independent signals in order to reconstruct the image data therefrom. In this case, by way of example, a local coil has three individually addressable coil elements that each have six possibly individually addressable reception antennas, which provides that in this example a local coil would then have 18 single reception antennas.

A multiplicity of such reception antennas may allow for faster MRT measurements by parallel imaging methods, for example. Therefore the higher the antenna density of the reception antennas, that is to say the number of reception antennas for the local coil, the higher the image quality and/or the faster the raw data acquisition. The problem is that the large number of reception antennas produce a large number of independent signals that need to be transmitted via a large number of cables and digitized via a large number of A/D converters (analog-digital converters).

The problem with signal selection devices from the prior art is that the digital selection chips need to have at least as many signal inputs for logical data streams as A/D converter chips, even if only a subset thereof is ever selected in all data capture situations. This requires a correspondingly large number of chips for the digital selection chips.

In MRT systems to date, the number of logical signal inputs of the digital selection chips has always been chosen to be the same as the logical number of signal inputs of the A/D converter chips. If the number of signal inputs of the digital selection chips may not be increased arbitrarily, the number of A/D converter chips is limited to the number of signal inputs of the digital selection chips. Multiplexing provides that the physical number may differ from the logical number. Multiplexing in the analog domain is independent of that in the digital domain and dynamic for each actual cable.

In MRT systems, it may be necessary for the number of logical data streams from the A/D converter chips to be larger than the number of logical data streams that may be captured simultaneously with the current data capture process (e.g., readout).

SUMMARY AND DESCRIPTION

The scope of the present invention is defined solely by the appended claims and is not affected to any degree by the statements within this summary. The present embodiments may obviate one or more of the drawbacks or limitations in the related art.

It is therefore an object of the present embodiments to limit the maximum number of signal inputs of the digital selection chips that may be captured simultaneously for the current data capture process (e.g., readout) so as to speed up MRT image production and to improve MRT image quality.

In certain embodiments, the signal selection device has a plurality of signal inputs for the reception of signals from the reception antennas, and also a plurality of signal outputs for the output of altered signals from the reception antennas. The signal selection device is used for selecting or reducing received signals from the reception antennas and for forwarding them to an image processing device. The signal selection device contains a plurality of A/D converter chips and a plurality of digital selection chips and also a control unit. The control unit may undertake exclusively tasks from the signal selection device, but may additionally also undertake other tasks, such as the control of the RF transmitters and the whole body coil, etc., so that the control unit may, in part, also be physically and/or logically arranged outside the reception device.

In certain embodiments, the received signals from the reception antennas are fed into the plurality of A/D converter chips via a plurality of signal inputs of the plurality of A/D converter chips, are converted into digital data streams therein, and are supplied to the digital selection chips via signal outputs of the A/D converter chips.

In certain embodiments, the digital selection chips perform selection/reduction of the logical data streams selected for the current data capture process, (e.g., what is known as a "readout"), using metadata from the control unit.

In certain embodiments, the actual A/D converter chips now perform selection and possibly reduction of the logical data streams selected for the current data capture process, (e.g., "readout"), using metadata from the control unit.

This allows the number of digital chips required to be reduced and production costs to be saved.

The data transmission from the A/D converter chips to the digital selection chips is thus intended to be organized such that only the logical data streams that are relevant to the current data capture process (e.g., readout) are ever transmitted. It is then possible for the number of inputs of the digital selection chips to be limited to the maximum number that may be captured simultaneously for a current readout. This number may be smaller than the number of logical data streams from the A/D converter chips.

To achieve this, the actual A/D converter chips need to perform a selection of the logical data streams selected for the current data capture process. For this, the A/D converter chips require appropriate metadata from the control unit for every current data capture process.

In this context, metadata are intended to be understood to refer to data that contain information about the raw data acquired in the current readout, such as information about the reception antennas used, in order to thus blindly convert the selection of an input cable for the reception antennas in the A/D converters instead, to date, of the signals from all the reception antennas. In connection with multiplexing, situations then also arise in which one physical cable provides a plurality of signals of which, potentially, only a subset is required, however. The situation becomes even more complex with the dynamic selection option for various mutually exclusive multiplexing methods per cable, only precisely one of which is active and the other logical data streams need to be transmitted to the digital selection chips too without such metadata. In particular, the metadata may contain channel selection information that may, for example, be in the form of a bit mask. In this context, each signal input (e.g., logical data stream) of the A/D converter chips has an associated explicit channel number. By way of example, counting is consecutive starting from 1 (e.g., 1, 2, 3, . . . ). In the channel selection bit mask, each channel number is assigned a bit. Once this has been set, the channel is relevant to the current data capture process and needs to be transmitted to the digital selection chips, otherwise it does not. For example, three logical data streams may reach the A/D converter via a shared cable. Either the first logical data stream on its own is active or alternatively the other two data streams, while the naive AD converter without meta information always needs to stolidly produce all three data streams and may thereby require an unnecessarily large number of digital selection chips that may never be used.

The number of inputs of the digital selection chips may be chosen to be smaller than the number of inputs of the (e.g., logical data streams) of the A/D converter chips. For a prescribed number of inputs of the digital selection chips, this allows MRT system configurations with a relatively high number of inputs of the A/D converter chips to be used.

In particular, the number of A/D converter chips may therefore also be larger than the number of digital selection chips. By way of example, it is thus possible for the number of A/D converter chips to be up to 50% larger than the number of digital selection chips.

A further issue is how the metadata get from the control unit to the A/D converter chips.

In an embodiment, the A/D converter chips and the digital selection chips have separate metadata inputs that may be used to input metadata from the control unit directly. This allows very simple, inexpensive, secure, and quick transfer of the metadata to the A/D converter chips and the digital selection chips to be effected, so that the image processing may take place quickly and at high quality. In particular, the metadata inputs of both chips are of similar or identical design and also transmit similar or identical metadata.

Alternatively or in addition to the embodiment specified above with the separate metadata inputs of the A/D converter chips, it is possible for at least one metadata channel (md4) to be arranged between each of the A/D converter chips and the associated digital selection chips and to be used to input the metadata from the control unit into the A/D converter chips indirectly via the digital selection chips. These metadata channels are, in particular, bidirectional data channels that may route data in both directions, namely the metadata in one direction and the digitized data stream from the reception antennas in the other direction. These indirect metadata channels between the digital selection chips and the A/D converter chips may also be unidirectional and may be provided just for the transmission of the metadata from the control unit to the A/D converter chips indirectly via the digital selection chips.

In the case of transmission of the metadata from the control unit to the A/D converter chips via the digital selection chips, the signal selection is transparent for the, (e.g., independently of the), remainder of the system components, particularly the control unit.

For all the variants described above, the signal selection device may have one or more signal distribution units that are arranged for signal routing purposes between the interface arrangement for reception antennas and the A/D converter chips. In this arrangement, the received signals from the reception antennas are passed to the A/D converter chips via the signal distribution unit, wherein the signal distribution unit receives metadata from the control unit via a metadata input for the purpose of selecting the received signals from the reception antennas and distributing them over the associated A/D converter chips.

In a further embodiment, particularly in the case of relatively small systems with just a few (e.g., up to 24) reception antennas, it is possible to dispense with a separate signal distribution unit for the signals from the reception antennas and for the signal reduction to be effected completely by the A/D converter chips. In addition, dispensing with a signal distribution unit it is also of interest to systems if full expansion is just around the corner, that is to say that a switching matrix has a similarly large number of active outputs to inputs, and thereby becomes internally very complex in respect of the number of switches.

The interface arrangement of the reception device may be located between the immobile signal selection device, (e.g., one permanently installed in the MRT system), of the system and the mobile local coil of the patient. Alternatively, it is also possible for the signal selection device to be included in the local coil, so that the interface arrangement is located between the local coil with the signal selection device and the image processing device. Alternatively, only portions of the signal selection device, (such as one or more of the control unit, the signal distribution unit, the A/D converter chips, and/or the digital selection chips), may be included in the local coil, so that the interface arrangement is located between the local coil with these portions of the signal selection device and the image processing device.

The aim of the present embodiments is therefore also to protect a local coil of the reception device for the reception of MRT signals that are transmitted from a body or body part of a patient, (e.g., in response to excitation signals from a whole body coil of the magnetic resonance imaging scanner (MRT)), wherein the local coil includes the signal selection device.

The aim of the present embodiments is also to protect a magnetic resonance imaging scanner (MRT) having a reception device that has at least one signal selection device, wherein the reception device is also able to be part of a local coil associated with the MRT.

The aim of the present embodiments is also to protect a method for signal transmission using at least one signal selection device or at least one local coil or a magnetic resonance imaging scanner (MRT).

DETAILED DESCRIPTION

FIGS. 1 to 4 each depict reception antennas (subsequently antennas for short) A1, A2, A3, A4, . . . , An that are coupled to the signal selection device 3. Antennas A1, A2 are part of a local coil 1, and the local coil 1 together with the signal selection device 3 are considered to be a reception device 2. The local coil 1 may also have a multiplicity of further standard components, such as preamplifiers, switch elements, or detuning devices for deactivating and activating the antennas A1, A2, A3, A4, . . . , An.

Figure 1:
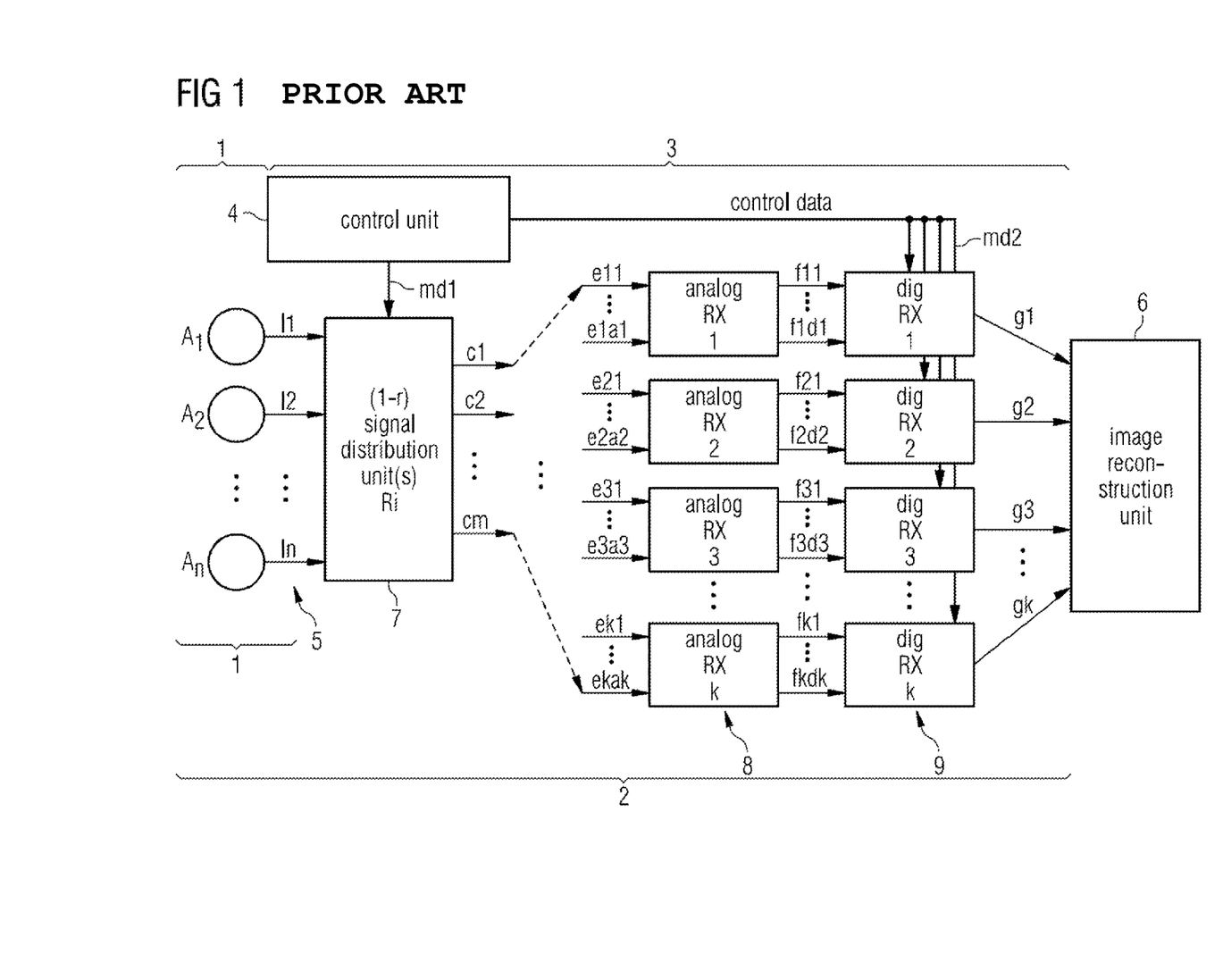
FIG. 1 schematically depicts a signal selection device according to the prior art within a reception device.

FIG. 1 depicts an overview of the reception path of a reception device 2 with at least one local coil 1 within an MRT system.

The reception device 2 contains the local coil 1 (of the patient) with a plurality of reception antennas A1, A2, . . . An and the further components thereof, (such as amplifiers, filters, etc.), as well as a signal distribution unit 7 (which may be permanently arranged in the system), a control unit 4, and a signal selection device 3. In this case, the control unit 4 may undertake exclusively tasks of the signal selection device 3, but may additionally also undertake other tasks, (such as the control of the RF transmitters and the whole body coil, etc.), so that the control unit 4 may, in part, also be physically and/or logically arranged outside the reception device 2.

The signal selection device 3 in turn contains a plurality of A/D converter chips 8 and also a plurality of digital selection chips 9, the number of A/D converter chips 8 in this case being equal to the number of digital selection chips 9.

An image processing device 6, which then calculates and reworks MRT images from the data for the signal selection device 3, and also possibly stores and/or visually outputs them using a display, is coupled to the reception device 2.

The reception antennas A1, A2, . . . An of the local coil 1 receive MRT signals, which are transmitted from a body or body part of a patient, for example, in response to excitation signals from a whole body coil of an MRT appliance. The signal outputs of the reception antennas A1, A2, . . . An of the local coil 1 are connected for signal routing purposes to signal inputs l1, l2, l3, . . . ln of the signal distribution unit 7 via an interface arrangement 5 (with suitable cable connections, for example). It is also possible for a plurality of signal distribution units 7 to be existent within this local coil 1 or a plurality of local coils 1.

This signal distribution unit 7 is used to perform selection and distribution of its input signals, or the output signals from the reception antennas of the local coil (e.g., the raw data), which reach the signal distribution unit 7 via the signal inputs l1, l2, l3, . . . ln, over the output signals that are output via its signal outputs c1, c2, c3, . . . cm. The number of signal inputs l1, l2, l3, . . . ln and the number of signal outputs c1, c2, c3, . . . cm may be the same, but it is also possible for a larger number of input signals than output signals to be existent, or vice versa.

The specific signal distribution is prescribed for the signal distribution unit 7 by the control unit 4 by what are known as metadata, (e.g., information about the raw data), using a data input md1 for metadata that is provided for this purpose.

Each output signal from the signal outputs c1, c2, c3, . . . cm of the signal distribution unit 7 may transmit the signals from a plurality of reception coil elements simultaneously or, depending on technical circumstances, also exclusively, e.g. by frequency-division multiplexing.

The signal outputs c1, c2, c3, . . . cm of the signal distribution unit 7 are connected for signal routing purposes to the signal inputs e11-e1a1, e21-e2a2, e31-e3a3, . . . ek1-ekak of a plurality of A/D converter chips 8 of the signal selection device 3.

The task of these A/D converter chips 8 is to take their plurality of input signals and extract the logical data streams from the individual reception antennas A1, A2, A3, . . . An and digitize them (e.g., sampling and conversion into a digital numerical sequence) and convert them into continuous data streams.

The signal outputs of the A/D converter chips f11-f1d1, f21-f2d2, f31-f3d3, . . . fk1-fkdk are connected to signal inputs similarly of a large number of digital selection chips 9. These digital selection chips 9 take the logical data streams and select the signals from those reception antennas A1, A2, A3, . . . An that have been selected for the current data capture process (e.g., readout). The information required for this is obtained by the digital selection chips 9 as metadata from the control unit 4 via a connection md2 provided for this purpose. The digital selection chips 9 combine the selected received signals into data units and transmit them as data packets via the signal outputs g1, g2, g3, . . . gk of a transmission channel 5 to the image processing device 6.

Figure 2:
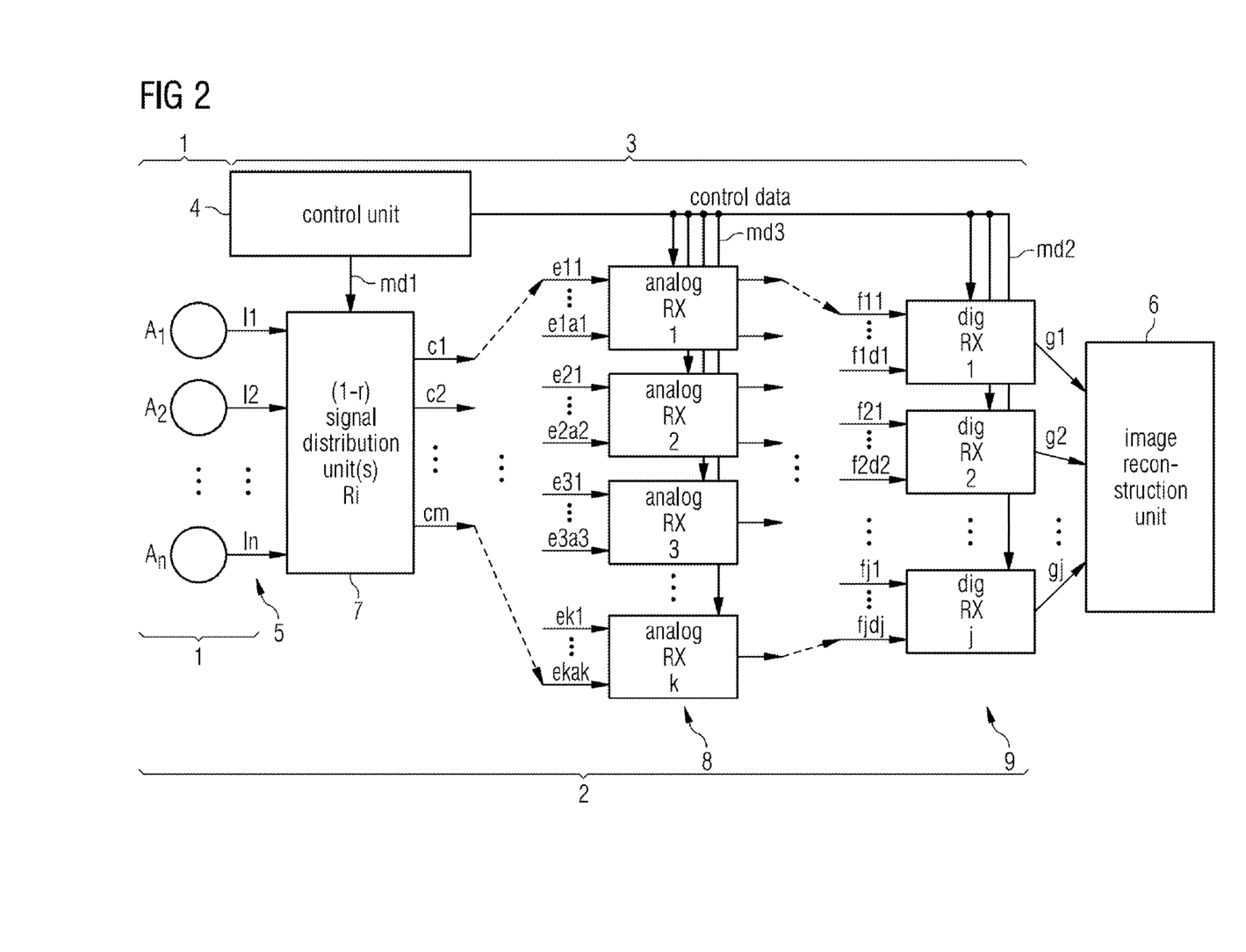
FIG. 2 schematically depicts a first embodiment of a signal selection device within a reception device.

FIG. 2 depicts a signal selection device 3, wherein the control unit 4 transmits the metadata directly to the A/D converter chips 8, to which end the A/D converter chips 8 have separate metadata inputs md3 for this purpose. The control unit 4 then transmits the ascertained metadata both to the digital selection chips 9 and to the A/D converter chips 8. FIG. 2 thus depicts signal selection in the A/D converter chips 8 with direct actuation by the control unit 4. Since the selection of the logical data streams used is now made in the actual A/D converter chips 8, the number of digital selection chips 9 may be chosen to be smaller in FIG. 2 than in the case of the conventional approach. In FIG. 2, the number of digital selection chips 9 is therefore smaller than the number of A/D converter chips 8. In FIG. 1, the number of digital selection chips 9 is the same as the number of A/D converter chips 8. Otherwise, the two embodiments in FIGS. 1 and 2 are identical (apart from the specially designed A/D converter chips 8).

Figure 3:
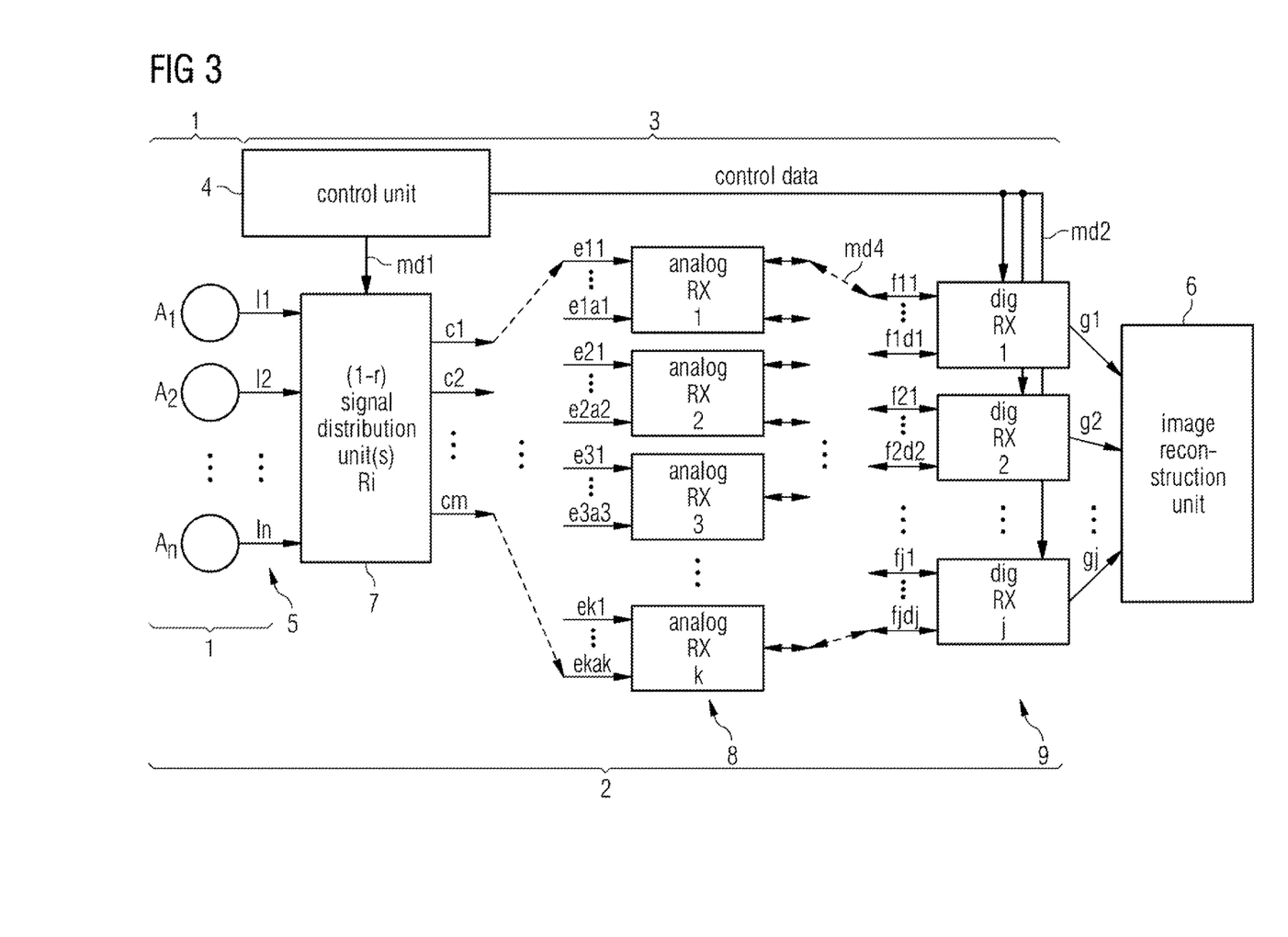
FIG. 3 schematically depicts a second embodiment of a signal selection device within a reception device.

In the embodiment in FIG. 3, in comparison with the embodiment in FIG. 1, there are additionally further indirect bidirectional metadata channels md4 provided via the digital selection chips 9 into the A/D converter chips 8, which provide that the number of digital selection chips 9 is also smaller in FIG. 3 than that in FIG. 1. In FIG. 3, the number of digital selection chips 9 is therefore likewise smaller than the number of A/D converter chips 8. Apart from the specially designed A/D converter chips 8 and the digital selection chips 9 with the bidirectional metadata channels md4 to the A/D converter chips 9, the two embodiments in FIGS. 1 and 3 are identical.

In this case, FIG. 3 depicts an embodiment with a bidirectional connection in the form of the metadata channels md4 between the A/D converter chips 8 and the associated digital selection chips 9. In this case, the digital selection chips 9 forward a portion of the metadata, which the digital selection chips 9 themselves have obtained from the control unit 4, via a communication link in the form of the metadata channels md4 to the A/D converter chips 8, without this requiring the collaboration of other components, particularly the control unit 4. Therefore, the method in this embodiment is transparent for the control unit 4, e.g., independent thereof. In this embodiment, the control unit 4 therefore does not need to have any direct metadata inputs into the A/D converter chips 8. FIG. 3 thus depicts a signal selection in the A/D converter chips 8 with local actuation by the digital selection chips 9 without the intervention of the control unit 4.

Instead of the bidirectional metadata channels md4, there may also be separate unidirectional metadata channels existent that may be used to transmit just metadata from the digital selection chips 9 into the A/D converter chips 8.

Figure 4:
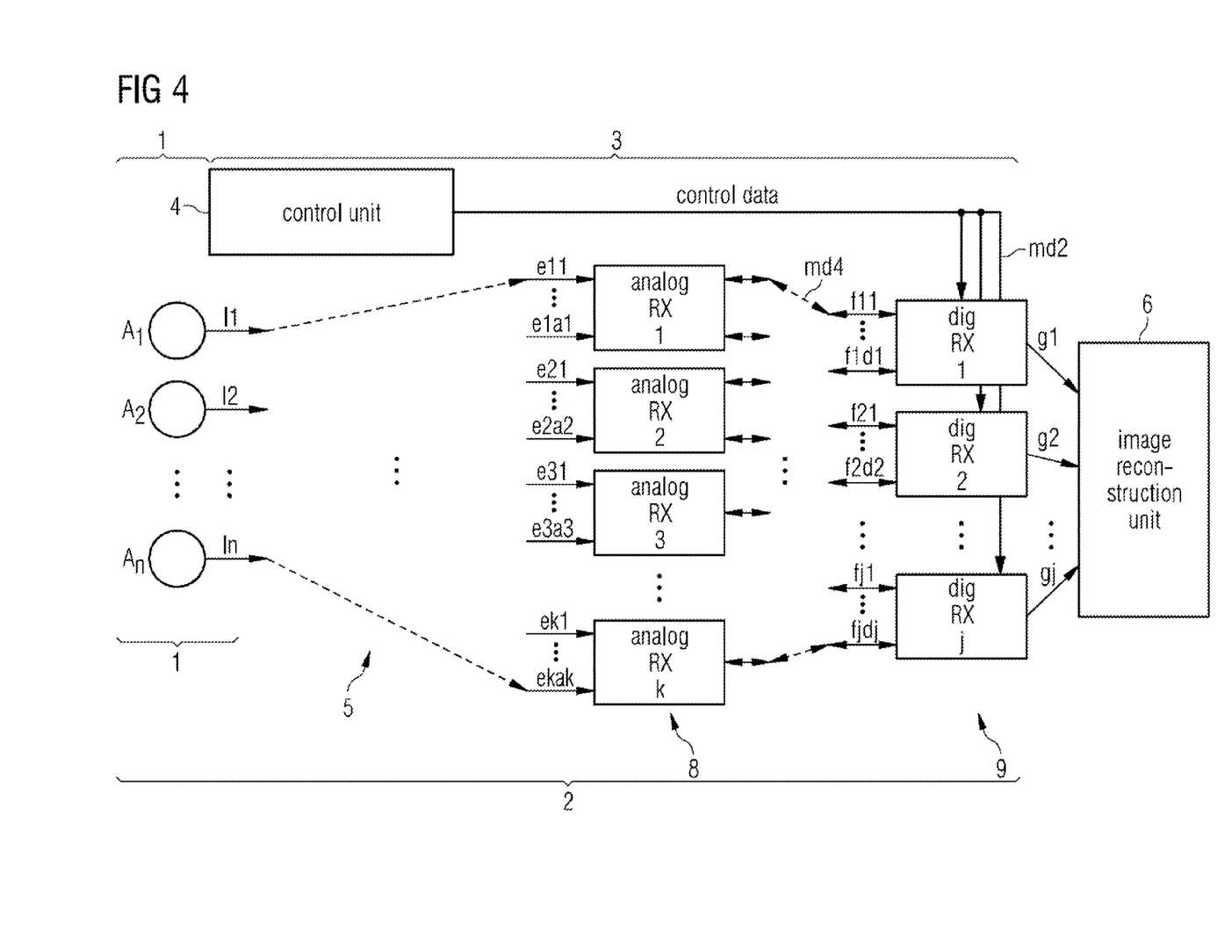
FIG. 4 schematically depicts a third embodiment of a signal selection device within a reception device.

In the embodiment depicted in FIG. 4, in comparison with the embodiment in FIG. 3, only the signal distribution unit 7 has been omitted. Otherwise, the two embodiments in FIGS. 3 and 4 are identical. It is also possible for the signal distribution unit 7 to be omitted in the embodiment depicted in FIG. 2, however.

In this case, FIG. 4 depicts a further embodiment particularly for system configurations with relatively few input signals from the reception antennas A1, A2, A3 . . . An, (e.g., in the case of smaller systems), in which the signal distribution unit 7 may be omitted. The signal selection then takes place in the A/D converter chips 8. In this case, additional A/D converter chips 8 are sometimes required in order to capture all the signals from the reception antennas A1, A2, A3 . . . An. FIG. 4 thus depicts signal selection in the A/D converter chips 8 with local actuation by the digital selection chips 9 without intervention by the control unit 4, but without a separate signal distribution unit 7.

The embodiments in FIGS. 2, 3 and 4 may be combined with one another as desired. Thus, by way of example, the embodiments in FIGS. 2 and 3 may be combined and hence the metadata inputs md1, md2, md3, and also the bidirectional metadata channel md4 may be existent, in which case the metadata for the A/D converter chips 8 may be provided arbitrarily directly via the metadata input md3 or indirectly via the bidirectional metadata channel md4. In this combination from FIGS. 2 and 3, but also in FIG. 2 itself, the signal distribution unit 7 may also be dispensed with, in a similar manner to FIG. 4.

Finally, it is pointed out once again that the detailed methods and apparatuses described above are exemplary embodiments and that the basic principle may also be varied by a person skilled in the art within broad realms without departing from the scope of the invention as prescribed by the claims. For the sake of completeness, it is also pointed out that the use of the indefinite article "a" or "an" does not preclude the features in question from being existent a plurality of times too. Similarly, the term "unit" or "chip" does not preclude these from including a plurality of components that may possibly also be distributed in space.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A signal selection device configured for selecting among local coil reception antennas of a reception device in a magnetic resonance imaging scanner, the signal selection device comprising:
   a control unit configured to provide metadata to at least one component of the signal selection device;
   a plurality of analog-digital (A/D) converter chips, wherein each A/D converter chip of the plurality of A/D converter chips comprises a plurality of signal inputs and a plurality of signal outputs, wherein the plurality of signal inputs is configured to receive signals from the local coil reception antennas via an interface arrangement, and wherein the plurality of signal outputs is configured to output altered signals from the local coil reception antennas via the same interface arrangement;
   a plurality of digital selection chips; and
   wherein the received signals from the local coil reception antennas are fed into the plurality of A/D converter chips via the plurality of signal inputs of the plurality of A/D converter chips;
   wherein the received signals are converted into at least two digital data streams by the plurality of A/D converter chips;
   wherein the plurality of A/D converter chips is configured to utilize metadata from the control unit when selecting a portion of the at least two digital data streams that is less than all of the digital data streams with the selected portion of the at least two digital data streams then being forwarded to an image processing device; and
   wherein the selected portion of the at least two digital data streams is supplied to the digital selection chips via the plurality of the signal outputs of the plurality of A/D converter chips.

2. The signal selection device as claimed in claim 1, wherein a total number of the plurality of A/D converter chips is larger than a total number of the plurality of digital selection chips.

3. The signal selection device as claimed in claim 2, wherein the plurality of A/D converter chips and the plurality of digital selection chips each comprise separate metadata inputs that are configured to input metadata from the control unit directly.

4. The signal selection device as claimed in claim 3,
   wherein at least one metadata channel is arranged between each A/D converter chip of the plurality of A/D converter chips and an associated digital selection chip of the plurality of digital selection chips; and
   wherein the at least one metadata channel is configured to input metadata from the control unit into the plurality of A/D converter chips indirectly via the plurality of digital selection chips.

5. The signal selection device as claimed in claim 4, further comprising a signal distribution unit arranged between the interface arrangement of the local coil reception antennas and the plurality of A/D converter chips;
   wherein the received signals from the local coil reception antennas are passed to the plurality of A/D converter chips via the signal distribution unit; and wherein the signal distribution unit is configured to receive metadata from the control unit via a metadata input in order to select the received signals from the local coil reception antennas and distribute the selected received signals over the associated A/D converter chips of the plurality of A/D converter chips.

6. The signal selection device as claimed in claim 5, wherein the interface arrangement of the reception device in the magnetic resonance imaging scanner is located between the signal selection device of the magnetic resonance imaging scanner and the local coil reception antennas.

7. The signal selection device as claimed in claim 3, further comprising a signal distribution unit arranged between the interface arrangement of the local coil reception antennas and the plurality of A/D converter chips;
wherein the received signals from the local coil reception antennas are passed to the plurality of A/D converter chips via the signal distribution unit;
wherein the signal distribution unit is configured to receive metadata from the control unit via a metadata input in order to select the received signals from the local coil reception antennas and distribute the selected received signals over the associated A/D converter chips of the plurality of A/D converter chips.

8. The signal selection device as claimed in claim 3, wherein the interface arrangement of the reception device in the magnetic resonance imaging scanner, is located between the signal selection device of the magnetic resonance imaging scanner and the local coil reception antennas.

9. The signal selection device as claimed in claim 2,
wherein at least one metadata channel is arranged between each A/D converter chip of the plurality of A/D converter chips and an associated digital selection chip of the plurality of digital selection chips; and
wherein the at least one metadata channel is configured to input metadata from the control unit into the plurality of A/D converter chips indirectly via the plurality of digital selection chips.

10. The signal selection device as claimed in claim 2, further comprising a signal distribution unit arranged between the interface arrangement of the local coil reception antennas and the plurality of A/D converter chips;
wherein the received signals from the local coil reception antennas are passed to the plurality of A/D converter chips via the signal distribution unit; and
wherein the signal distribution unit is configured to receive metadata from the control unit via a metadata input in order to select the received signals from the local coil reception antennas and distribute the selected received signals over the associated A/D converter chips of the plurality of A/D converter chips.

11. The signal selection device as claimed in claim 2, wherein the interface arrangement of the reception device in the magnetic resonance imaging scanner is located between the signal selection device of the magnetic resonance imaging scanner and the local coil reception antennas.

12. The signal selection device as claimed in claim 1, wherein the plurality of A/D converter chips and the plurality of digital selection chips each comprise separate metadata inputs that are configured to input metadata from the control unit directly.

13. The signal selection device as claimed in claim 1, wherein at least one metadata channel is arranged between each A/D converter chip of the plurality of A/D converter chips and an associated digital selection chip of the plurality of digital selection chips; and
wherein the at least one metadata channel is configured to input metadata from the control unit into the plurality of A/D converter chips indirectly via the plurality of digital selection chips.

14. The signal selection device as claimed in claim 13, wherein the at least one metadata channel is a bidirectional data channel that is configured to route data in both directions, whereby the metadata is routed in a first direction and a digitized data stream from the local coil reception antennas is routed in a second, opposite direction.

15. The signal selection device as claimed in claim 1, further comprising a signal distribution unit arranged between the interface arrangement of the local coil reception antennas and the plurality of A/D converter chips;
wherein the received signals from the local coil reception antennas are passed to the plurality of A/D converter chips via the signal distribution unit; and
wherein the signal distribution unit is configured to receive metadata from the control unit via a metadata input in order to select the received signals from the local coil reception antennas and distribute the selected received signals from the local coil reception antennas over the associated A/D converter chips of the plurality of A/D converter chips.

16. The signal selection device as claimed in claim 1, wherein the interface arrangement of the reception device in the magnetic resonance imaging scanner, is located between the signal selection device of the magnetic resonance imaging scanner and the local coil reception antennas.

17. A local coil reception antenna compatible with a magnetic resonance imaging scanner, the local coil reception antenna comprising:
a signal selection device comprising:
a control unit configured to provide metadata to at least one component of the signal selection device;
a plurality of analog-digital (A/D) converter chips, wherein each A/D converter chip of the plurality of A/D converter chips comprises a plurality of signal inputs and a plurality of signal outputs, wherein the plurality of signal inputs is configured to receive signals from the local coil reception antenna via an interface arrangement, and wherein the plurality of signal outputs is configured to output altered signals from the local coil reception antenna via the same interface arrangement; and
a plurality of digital selection chips;
wherein the received signals from the local coil reception antenna are fed into the plurality of A/D converter chips via the plurality of signal inputs of the plurality of A/D converter chips;
wherein the received signals are converted into at least two digital data streams by the plurality of A/D converter chips;
wherein the plurality of A/D converter chips is configured to utilize metadata from the control unit when selecting a portion of the at least two digital data streams that is less than all of the digital data streams with the selected portion of the at least two digital data streams then being forwarded to an image processing device; and
wherein the selected portion of the at least two digital data streams is supplied to the digital selection chips via the plurality of signal outputs of the plurality of the A/D converter chips; and
wherein the local coil reception antenna is configured to receive magnetic resonance transmission signals that are transmitted from a body or body part of a patient in response to excitation signals sent from a whole body coil of the magnetic resonance imaging scanner, when the signal selection device selects the local coil reception antenna as an active reception antenna of the magnetic resonance imaging scanner.

18. A magnetic resonance imaging scanner comprising:
a reception device having a signal selection device that is configured for selecting among local coil reception antennas in the magnetic resonance imaging scanner, the signal selection device comprising:
- a control unit configured to provide metadata to at least one component of the signal selection device;
- a plurality of analog-digital (A/D) converter chips, wherein each A/D converter chip of the plurality of A/D converter chips comprises a plurality of signal inputs and a plurality of signal outputs, wherein the plurality of signal inputs is configured to receive signals from the local coil reception antennas via an interface arrangement, and wherein the plurality of signal outputs is configured to output altered signals from the local coil reception antennas via the same interface arrangement; and
- a plurality of digital selection chips;
wherein the received signals from the local coil reception antennas are fed into the plurality of A/D converter chips via the plurality of signal inputs of the plurality of A/D converter chips;
wherein the received signals are converted into at least two digital data streams by the plurality of A/D converter chips;
wherein the plurality of A/D converter chips is configured to utilize metadata from the control unit to select a portion of the at least two digital data streams that is less than all of the digital data streams with the selected portion of the at least two digital data streams then being forwarded to an image processing device; and
wherein the selected portion of the at least two digital data streams is supplied to the digital selection chips via the plurality of the signal outputs of the plurality of A/D converter chips.

* * * * *